US012594269B2

(12) United States Patent
Rogge et al.

(10) Patent No.: US 12,594,269 B2
(45) Date of Patent: Apr. 7, 2026

(54) METHOD FOR ENHANCING THE PHARMACOKINETICS OR INCREASING THE PLASMA CONCENTRATION OF METHYL 3-((METHYLSULFONYL)AMINO)-2-(((4-PHENYLCYCLOHEXYL)OXY)METHYL)PIPERIDINE-1-CARBOXYLATE OR A SALT THEREOF WITH AN INHIBITOR OF CYTOCHROME P450

(71) Applicant: TAKEDA PHARMACEUTICAL COMPANY LIMITED, Osaka (JP)

(72) Inventors: Mark Rogge, Cambridge, MA (US); Hélène Faessel, Cambridge, MA (US); Hong Lu, Cambridge, MA (US); Karthik Venkatakrishnan, Cambridge, MA (US); Liming Zhang, Cambridge, MA (US); John Wagner, Cambridge, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 923 days.

(21) Appl. No.: 17/791,302

(22) PCT Filed: Jan. 7, 2021

(86) PCT No.: PCT/US2021/012447
§ 371 (c)(1),
(2) Date: Jul. 7, 2022

(87) PCT Pub. No.: WO2021/142083
PCT Pub. Date: Jul. 15, 2021

(65) Prior Publication Data
US 2023/0029486 A1 Feb. 2, 2023

Related U.S. Application Data

(60) Provisional application No. 62/959,514, filed on Jan. 10, 2020.

(51) Int. Cl.
| A61K 31/445 | (2006.01) |
| A61K 9/00 | (2006.01) |
| A61K 31/425 | (2006.01) |
| A61K 31/5377 | (2006.01) |

(52) U.S. Cl.
CPC .......... *A61K 31/445* (2013.01); *A61K 9/0056* (2013.01); *A61K 31/425* (2013.01); *A61K 31/5377* (2013.01)

(58) Field of Classification Search
CPC .................................................. A61K 31/445
See application file for complete search history.

(56) References Cited

U.S. PATENT DOCUMENTS

| 10,287,305 B2 | 5/2019 | Fujimoto et al. |
| 10,508,083 B2 | 12/2019 | Fujimoto et al. |
| 10,898,737 B2 | 1/2021 | Fujimoto et al. |
| 11,292,766 B2 | 4/2022 | Fujimoto et al. |
| 2022/0081399 A1 | 3/2022 | Fujimoto et al. |

FOREIGN PATENT DOCUMENTS

| JP | 2016512549 A | 4/2016 |
| JP | 2019504098 A | 2/2019 |
| JP | 2019524777 A | 9/2019 |
| WO | WO-2002020020 A1 | 3/2002 |
| WO | WO 2014/159745 A1 | 10/2014 |
| WO | WO 2017/135306 A1 | 8/2017 |
| WO | WO-2018026835 A1 | 2/2018 |
| WO | WO 2021/048821 A1 | 3/2021 |
| WO | WO 2021/048822 A1 | 3/2021 |

OTHER PUBLICATIONS

Boof, M. et al., European Journal of Clinical Pharmacology, 2019, 75, 195-205 (Year: 2019).*
Medsafe. Drug Metabolism—The Importance of Cytochrome P450 3A4. New Zealand Medicines and Medical Devices Safety Authority. Mar. 6, 2014. https://www.medsafe.govt.nz/profs/puarticles/march2014drugmetabolismcytochromep4503a4.htm, accessed Jun. 13, 2025 (Year: 2014).*
Hossain, M.A. et al., Journal of Pharmacy and Pharmacology, 2017, 69, 1786-1793 (Year: 2017).*
International Search Report and Written Opinion for International Application No. PCT/US2021/012447, European Patent Office, Netherlands, mailed on Apr. 21, 2021, 10 pages.
Boof, M.L., et al., "Interaction potential of the dual orexin receptor antagonist ACT-541468 with CYP3A4 and food: results from two interaction studies," *Eur. J. Clin. Pharmacol.* 75(2):195-205, Springer Science+Business Media, Berlin, Germany (2019).
Dingemanse, J., et al., "Pharmacokinetic interactions between the orexin receptor antagonist almorexant and the CYP3A4 inhibitors ketoconazole and diltiazem," *J. Pharm. Sci.* 103(5):1548-1556, Elsevier, Netherlands (2014).
Hossain, M., et al., "Inhibition of human cytochromes P450 in vitro by ritonavir and cobicistat," J Pharm Pharmacol 69(12):1786-1793, Oxford University Press, United Kingdom (Dec. 2017).
Cato III, A., et al., "The effect of multiple doses of ritonavir on the pharmacokinetics of rifabutin," Clin Pharmacol Ther 63(4):414-21, Wiley, United States (Apr. 1998).
English language translation of Office Action and Search Report for Russian Application No. 2022121500, dated Jun. 11, 2024, 9 pages.
Zhang, Z., et al., "Drug metabolism in drug discovery and development," Acta Pharmaceutica Sinica B 8(5):721-732, Elsevier B.V., China (Sep. 2018).

(Continued)

*Primary Examiner* — John S Kenyon
*Assistant Examiner* — Sara Elizabeth Bell
(74) *Attorney, Agent, or Firm* — Sterne, Kessler, Goldstein & Fox P.L.L.C.

(57) ABSTRACT

Described herein are compositions comprising (a) methyl 3-((methyl sulfonyl)amino)-2-(((4-phenylcyclohexyl)oxy) methyl) piperidine-1-carboxy late or a salt thereof; and (b) an agent for reducing metabolism of (a) and uses thereof.

18 Claims, 3 Drawing Sheets

(56)                    References Cited

OTHER PUBLICATIONS

U.S. Department of Health and Human Services, "In Vitro Drug
Interaction Studies—Cytochrome P450 Enzyme- and Transporter-
Mediated Drug Interactions Guidance for Industry," Center for Drug
Evaluation and Research—Food and Drug Administration, pub-
lished Jan. 2020, 46 pages.

* cited by examiner

METHOD FOR ENHANCING THE PHARMACOKINETICS OR INCREASING THE PLASMA CONCENTRATION OF METHYL 3-((METHYLSULFONYL)AMINO)-2-(((4-PHENYLCYCLOHEXYL)OXY)METHYL) PIPERIDINE-1-CARBOXYLATE OR A SALT THEREOF WITH AN INHIBITOR OF CYTOCHROME P450

CROSS-REFERENCE TO RELATED APPLICATIONS

This application claims priority to U.S. Provisional Application No. 62/959,514 filed Jan. 10, 2020, the entire contents of which are incorporated herein by reference in its entirety.

BACKGROUND OF THE INVENTION

Orexin (OX) is a neuropeptide which regulates sleep/wakefulness and is implicated in energy homeostasis, mood, stress, and reward through activation of two G-protein coupled receptors, OX1R and OX2R. OX2R agonists directly target the underlying disease pathophysiology of Narcolepsy Type 1 (NT1) by restoring OX2R receptor signaling in these patients, who lack intrinsic OX. Methyl 3-((methylsulfonyl)amino)-2-(((4-phenylcyclohexyl)oxy) methyl) piperidine-1-carboxylate showed significant effects on improving wakefulness and reducing cataplexy-like symptoms in a rodent model of narcolepsy, and promoted wakefulness in both healthy mice and nonhuman primates. Methyl 3-((methylsulfonyl)amino)-2-(((4-phenylcyclohexyl)oxy)methyl) piperidine-1-carboxylate is the first OX2R agonist to have entered human studies, and was shown to be safe and well-tolerated when administered intravenously (IV) in single dose studies in both healthy volunteers and NT1 patients.

SUMMARY OF THE INVENTION

One embodiment is a combination therapy comprising (a) an orexin 2 receptor (OX2R) agonist; and (b) an agent for reducing metabolism of the OX2R agonist, compositions and kits comprising the combination therapy, and methods of using the combination therapy.

Another embodiment is a method for enhancing the pharmacokinetics of methyl 3-((methylsulfonyl)amino)-2-(((4-phenylcyclohexyl)oxy)methyl) piperidine-1-carboxylate or a salt thereof, comprising administering to a subject (a) methyl 3-((methylsulfonyl) amino)-2-(((4-phenylcyclohexyl)oxy)methyl) piperidine-1-carboxylate or a salt thereof; and (b) an agent for reducing metabolism of (a).

Another embodiment is a method for increasing the plasma concentration of methyl 3-((methylsulfonyl)amino)-2-(((4-phenylcyclohexyl)oxy)methyl) piperidine-1-carboxylate or a salt thereof, comprising administering to a subject (a) methyl 3-((methylsulfonyl)amino)-2-(((4-phenylcyclohexyl)oxy)methyl) piperidine-1-carboxylate or a salt thereof; and (b) an agent for reducing metabolism of (a).

Another embodiment is a method for increasing wakefulness or decreasing excessive sleepiness in a subject in need thereof, comprising administering to the subject (a) methyl 3-((methylsulfonyl)amino)-2-(((4-phenylcyclohexyl)oxy) methyl) piperidine-1-carboxylate or a salt thereof; and (b) an agent for reducing metabolism of (a).

Another embodiment is a pharmaceutical composition comprising (a) methyl 3-((methylsulfonyl)amino)-2-(((4- phenylcyclohexyl)oxy)methyl) piperidine-1-carboxylate or a salt thereof; and (b) an agent for reducing metabolism of (a).

DETAILED DESCRIPTION OF THE INVENTION

Figure 1:
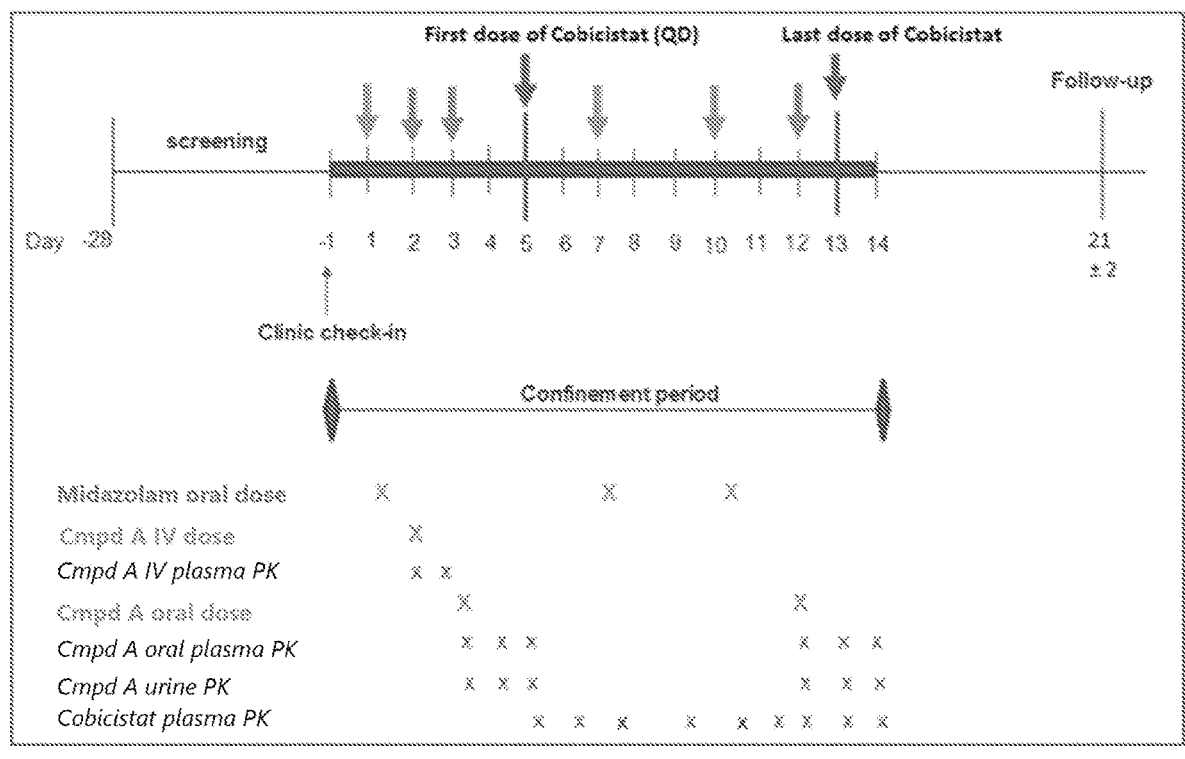
FIG. 1 shows the study schematic of Example 1.

Disclosed herein are combination therapies comprising (a) an orexin 2 receptor (OX2R) agonist; and (b) an agent for reducing metabolism of the OX2R agonist, compositions and kits comprising the combination therapy, and methods of using the combination therapy. Suitable OX2R agonists include but are not limited to those disclosed in WO2017/135306, the contents of which are hereby incorporated by reference.

Disclosed herein are combination therapies comprising (a) methyl 3-((methylsulfonyl)amino)-2-(((4-phenylcyclohexyl)oxy)methyl) piperidine-1-carboxylate or a salt thereof (hereafter "Compound (I)"); and (b) an agent for reducing metabolism of Compound (I), compositions and kits comprising the combination therapy, and methods of using the combination therapy. The present invention may improve the bioavailability in particular of methyl 3-((methylsulfonyl)amino)-2-(((4-phenylcyclohexyl)oxy)methyl) piperidine-1-carboxylate, which has an extensive first-pass metabolism.

The methods, compositions and uses disclosed herein include treating diseases or disorders or symptoms associated with excessive sleepiness in a subject in need thereof, as well as treating subjects suffering from excessive sleepiness who have not been diagnosed with any disease or disorder. Multiple causes have been attributed to excessive sleepiness, which include but are not limited to abnormal sleep quantity or sleep quality, as well as neurological, psychological, cardiac, and pulmonary disorders.

In an embodiment, the methods, compositions and uses of this disclosure may be directed to treating excessive sleepiness caused by lack of the neuropeptide OX that regulates arousal, wakefulness, and appetite. Excessive sleepiness can also occur in individuals who do not have deficiency of orexin. This disclosure is also directed to treating diseases, disorders, and/or symptoms of excessive sleepiness that are not associated with reduced orexin level.

Disclosed herein are methods for enhancing the pharmacokinetics of Compound (I), comprising administering to a subject (a) Compound (I); and (b) an agent for reducing metabolism of Compound (I).

Further disclosed herein is a combination therapy comprising (a) Compound (I); and (b) an agent for reducing metabolism of Compound (I) for use in enhancing the pharmacokinetics of Compound (I).

Further disclosed herein are uses of (a) Compound (I); and (b) an agent for reducing metabolism of Compound (I) in the manufacture of a medicament for enhancing the pharmacokinetics of Compound (I).

Further disclosed herein is an agent for reducing metabolism of Compound (I) for use in enhancing the pharmacokinetics of Compound (I).

Further disclosed herein is a use of an agent for reducing metabolism of Compound (I) in the manufacture of a medicament for enhancing the pharmacokinetics of Compound (I).

Disclosed herein are methods for increasing the plasma concentration of Compound (I), comprising administering to a subject (a) Compound (I); and (b) an agent for reducing metabolism of Compound (I).

Further disclosed herein is a combination therapy comprising (a) Compound (I); and (b) an agent for reducing metabolism of Compound (I) for use in increasing the plasma concentration of Compound (I).

Further disclosed herein are uses of (a) Compound (I); and (b) an agent for reducing metabolism of Compound (I) in the manufacture of a medicament for increasing the plasma concentration of Compound (I).

Further disclosed herein is an agent for reducing metabolism of Compound (I) for use in increasing the plasma concentration of Compound (I).

Further disclosed herein is a use of an agent for reducing metabolism of Compound (I) in the manufacture of a medicament for increasing the plasma concentration of Compound (I).

Disclosed herein are methods for maintaining the pharmaceutical effect of Compound (I) comprising administering to a subject (a) Compound (I); and (b) an agent for reducing metabolism of Compound (I).

Further disclosed herein is a combination therapy comprising (a) Compound (I); and (b) an agent for reducing metabolism of Compound (I) for use in maintaining the pharmaceutical effect of Compound (I).

Further disclosed herein are uses of (a) Compound (I); and (b) an agent for reducing metabolism of Compound (I) in the manufacture of a medicament for maintaining the pharmaceutical effect of Compound (I).

Disclosed herein are methods for maintaining the pharmaceutically effective plasma concentration of Compound (I), comprising administering to a subject (a) Compound (I); and (b) an agent for reducing metabolism of Compound (I).

Further disclosed herein is a combination therapy comprising (a) Compound (I); and (b) an agent for reducing metabolism of Compound (I) for use in maintaining the pharmaceutically effective plasma concentration of Compound (I).

Further disclosed herein are uses of (a) Compound (I); and (b) an agent for reducing metabolism of Compound (I) in the manufacture of a medicament for maintaining the pharmaceutically effective plasma concentration of Compound (I).

Disclosed herein are methods for reducing metabolism of Compound (I) comprising administering to a subject (a) Compound (I); and (b) a CYP3A inhibitor.

Further disclosed herein is a combination therapy comprising (a) Compound (I); and (b) a CYP3A inhibitor for use in reducing metabolism of Compound (I).

Further disclosed herein are uses of (a) Compound (I); and (b) a CYP3A inhibitor in the manufacture of a medicament for reducing metabolism of Compound (I).

Disclosed herein are methods for reducing a time-dependent decrease in the plasma concentration of Compound (I) comprising administering to a subject (a) Compound (I); and (b) a CYP3A inhibitor.

Further disclosed herein is a combination therapy comprising (a) Compound (I); and (b) a CYP3A inhibitor for use in reducing a time-dependent decrease in the plasma concentration of Compound (I).

Further disclosed herein are uses of (a) Compound (I); and (b) a CYP3A inhibitor in the manufacture of a medicament for reducing a time-dependent decrease in the plasma concentration of Compound (I).

Disclosed herein are methods for reducing metabolism of Compound (I) comprising administering to a subject (a) Compound (I); and (b) a CYP3A4 inhibitor.

Further disclosed herein is a combination therapy comprising (a) Compound (I); and (b) a CYP3A4 inhibitor for use in reducing metabolism of Compound (I).

Further disclosed herein are uses of (a) Compound (I); and (b) a CYP3A4 inhibitor in the manufacture of a medicament for reducing metabolism of Compound (I).

Disclosed herein are methods for reducing a time-dependent decrease in the plasma concentration of Compound (I) comprising administering to a subject (a) Compound (I); and (b) a CYP3A4 inhibitor.

Further disclosed herein is a combination therapy comprising (a) Compound (I); and (b) a CYP3A4 inhibitor for use in reducing a time-dependent decrease in the plasma concentration of Compound (I).

Further disclosed herein are uses of (a) Compound (I); and (b) a CYP3A4 inhibitor in the manufacture of a medicament for reducing a time-dependent decrease in the plasma concentration of Compound (I).

Disclosed herein are methods for increasing wakefulness in a subject in need thereof, comprising administering to the subject (a) Compound (I); and (b) an agent for reducing metabolism of Compound (I).

Further disclosed herein is a combination therapy comprising (a) Compound (I); and (b) an agent for reducing metabolism of Compound (I) for use in increasing wakefulness in a subject.

Further disclosed herein are uses of (a) methyl 3-((methylsulfonyl)amino)-2-(((4-phenylcyclohexyl)oxy)methyl) piperidine-1-carboxylate (Compound (I)), or a salt thereof; and (b) an agent for reducing metabolism of Compound (I) in the manufacture of a medicament for increasing wakefulness.

Disclosed here are methods for decreasing excessive sleepiness in a subject in need thereof, comprising administering to the subject (a) Compound (I); and (b) an agent for reducing metabolism of Compound (I).

Further disclosed herein is a combination therapy comprising (a) Compound (I); and (b) an agent for reducing metabolism of Compound (I) for use in decreasing excessive sleepiness in a subject.

Further disclosed herein are uses of (a) Compound (I); and (b) an agent for reducing metabolism of Compound (I) in the manufacture of a medicament for decreasing excessive sleepiness in a subject.

Disclosed herein are methods for treating excessive sleepiness in a subject in need thereof, comprising administering to the subject (a) Compound (I); and (b) an agent for reducing metabolism of Compound (I).

Further disclosed herein is a combination therapy comprising (a) Compound (I); and (b) an agent for reducing metabolism of Compound (I) for use in treating excessive sleepiness in a subject.

Further disclosed herein are uses of (a) Compound (I); and (b) an agent for reducing metabolism of Compound (I) in the manufacture of a medicament for treating excessive sleepiness.

Disclosed herein are methods for treating narcolepsy type 1 in a subject in need thereof, comprising administering to the subject (a) Compound (I); and (b) an agent for reducing metabolism of Compound (I).

Further disclosed herein is a combination therapy comprising (a) Compound (I); and (b) an agent for reducing metabolism of Compound (I) for use in treating narcolepsy type 1 in a subject in need thereof.

Disclosed herein are uses of (a) Compound (I); and (b) an agent for reducing metabolism of Compound (I) in the manufacture of a medicament for treating narcolepsy type 1 in a subject in need thereof.

Alternatively, disclosed herein are the method for decreasing a cataplexy-like event (e.g., cataplexy) in a subject in need thereof, comprising administering to the subject (a) Compound (I); and (b) an agent for reducing metabolism of Compound (I). In some embodiments, the subject is suffering from or diagnosed as narcolepsy type 1. In some embodiments, the cataplexy-like event is cataplexy.

Further disclosed herein is a combination therapy comprising (a) Compound (I); and (b) an agent for reducing metabolism of Compound (I) for use in decreasing a cataplexy-like event (e.g., cataplexy) in a subject in need thereof. In some embodiments, the subject is suffering from or diagnosed as narcolepsy type 1. In some embodiments, the cataplexy-like event is cataplexy.

Disclosed herein are uses of (a) Compound (I); and (b) an agent for reducing metabolism of Compound (I) in the manufacture of a medicament for decreasing a cataplexy-like event (e.g., cataplexy) in a subject in need thereof. In some embodiments, the subject is suffering from or diagnosed as narcolepsy type 1. In some embodiments, the cataplexy-like event is cataplexy.

Disclosed herein are methods for treating shift work disorder, shift work sleep disorder or jet lag syndrome in a subject in need thereof, comprising administering to the subject (a) Compound (I); and (b) an agent for reducing metabolism of Compound (I).

Further disclosed herein is a combination therapy comprising (a) Compound (I); and (b) an agent for reducing metabolism of Compound (I) for use in treating shift work disorder, shift work sleep disorder or jet lag syndrome in a subject in need thereof.

Disclosed herein are uses of (a) Compound (I); and (b) an agent for reducing metabolism of Compound (I) in the manufacture of a medicament for treating shift work disorder, shift work sleep disorder or jet lag syndrome in a subject in need thereof.

Disclosed herein are methods for enhancing the pharmacokinetics of an orexin 2 receptor (OX2R) agonist, comprising administering to a subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in enhancing the pharmacokinetics of the OX2R agonist.

Further disclosed herein are uses of (a) an orexin 2 receptor (OX2R) agonist; and (b) an agent for reducing metabolism of the OX2R agonist in the manufacture of a medicament for enhancing the pharmacokinetics of the OX2R agonist.

Further disclosed herein is an agent for reducing metabolism of an OX2R agonist for use in enhancing the pharmacokinetics of the OX2R agonist.

Further disclosed herein is a use of an agent for reducing metabolism of an OX2R agonist in the manufacture of a medicament for enhancing the pharmacokinetics of the OX2R agonist.

Disclosed herein are methods for increasing the plasma concentration of an orexin 2 receptor (OX2R) agonist, comprising administering to a subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in increasing the plasma concentration of the OX2R agonist.

Further disclosed herein are uses of (a) an orexin 2 receptor (OX2R) agonist; and (b) an agent for reducing metabolism of the OX2R agonist in the manufacture of a medicament for increasing the plasma concentration of the OX2R agonist.

Further disclosed herein is an agent for reducing metabolism of an OX2R agonist for use in increasing the plasma concentration of the OX2R agonist.

Further disclosed herein is a use of an agent for reducing metabolism of an OX2R agonist in the manufacture of a medicament for increasing the plasma concentration of the OX2R agonist.

Disclosed herein are methods for maintaining the pharmaceutical effect of an orexin 2 receptor (OX2R) agonist, comprising administering to a subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in maintaining the pharmaceutical effect of the OX2R agonist.

Further disclosed herein are uses of (a) an orexin 2 receptor (OX2R) agonist; and (b) an agent for reducing metabolism of the OX2R agonist in the manufacture of a medicament for maintaining the pharmaceutical effect of the OX2R agonist.

Disclosed herein are methods for maintaining the pharmaceutically effective plasma concentration of an orexin 2 receptor (OX2R) agonist, comprising administering to a subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in maintaining the pharmaceutically effective plasma concentration of the OX2R agonist.

Further disclosed herein are uses of (a) an orexin 2 receptor (OX2R) agonist; and (b) an agent for reducing metabolism of the OX2R agonist in the manufacture of a medicament for maintaining the pharmaceutically effective plasma concentration of the OX2R agonist.

Disclosed herein are methods for reducing metabolism of an orexin 2 receptor (OX2R) agonist, comprising administering to a subject (a) an orexin 2 receptor (OX2R) agonist; and (b) a CYP3A4 inhibitor.

Further disclosed herein is a combination therapy comprising (a) an orexin 2 receptor (OX2R) agonist; and (b) a CYP3A4 inhibitor for use in reducing metabolism of the OX2R agonist.

Further disclosed herein are uses of (a) an orexin 2 receptor (OX2R) agonist; and (b) a CYP3A4 inhibitor in the manufacture of a medicament for reducing metabolism of the OX2R agonist.

Disclosed herein are methods for reducing a time-dependent decrease in the plasma concentration of an orexin 2 receptor (OX2R) agonist comprising administering to a subject (a) an orexin 2 receptor (OX2R) agonist; and (b) a CYP3A4 inhibitor.

Further disclosed herein is a combination therapy comprising (a) an orexin 2 receptor (OX2R) agonist; and (b) a CYP3A4 inhibitor for use in reducing a time-dependent decrease in the plasma concentration of the OX2R agonist.

Further disclosed herein are uses of (a) an orexin 2 receptor (OX2R) agonist; and (b) a CYP3A4 inhibitor in the manufacture of a medicament for reducing a time-dependent decrease in the plasma concentration of the OX2R agonist.

Disclosed herein are methods for increasing wakefulness in a subject in need thereof, comprising administering to the subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in increasing wakefulness in a subject.

Further disclosed herein are uses of (a) an orexin 2 receptor (OX2R) agonist; and (b) an agent for reducing metabolism of the OX2R agonist in the manufacture of a medicament for increasing wakefulness.

Disclosed here are methods for decreasing excessive sleepiness in a subject in need thereof, comprising administering to the subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in decreasing excessive sleepiness in a subject.

Further disclosed herein are uses of (a) an orexin 2 receptor (OX2R) agonist; and (b) an agent for reducing metabolism of the OX2R agonist in the manufacture of a medicament for decreasing excessive sleepiness in a subject.

Disclosed here are methods for treating excessive sleepiness in a subject in need thereof, comprising administering to the subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in treating excessive sleepiness in a subject.

Further disclosed herein are uses of (a) an orexin 2 receptor (OX2R) agonist; and (b) an agent for reducing metabolism of the OX2R agonist in the manufacture of a medicament for treating excessive sleepiness.

Disclosed herein are methods for treating narcolepsy type 1 in a subject in need thereof, comprising administering to the subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in treating narcolepsy type 1 in a subject in need thereof.

Disclosed herein are uses of (a) an orexin 2 receptor (OX2R) agonist; and (b) an agent for reducing metabolism of the OX2R agonist in the manufacture of a medicament for treating narcolepsy type 1 in a subject in need thereof.

Alternatively, disclosed herein are the method for decreasing a cataplexy-like event (e.g., cataplexy) in a subject in need thereof, comprising administering to the subject (a) an orexin 2 receptor (OX2R) agonist; and (b) an agent for reducing metabolism of the OX2R agonist. In some embodiments, the subject is suffering from or diagnosed as narcolepsy type 1. In some embodiments, the cataplexy-like event is cataplexy.

Further disclosed herein is a combination therapy comprising (a) an orexin 2 receptor (OX2R) agonist; and (b) an agent for reducing metabolism of the OX2R agonist for use in decreasing a cataplexy-like event (e.g., cataplexy) in a subject in need thereof. In some embodiments, the subject is suffering from or diagnosed as narcolepsy type 1. In some embodiments, the cataplexy-like event is cataplexy.

Disclosed herein are uses of (a) an orexin 2 receptor (OX2R) agonist; and (b) an agent for reducing metabolism of the OX2R agonist in the manufacture of a medicament for decreasing a cataplexy-like event (e.g., cataplexy) in a subject in need thereof. In some embodiments, the subject is suffering from or diagnosed as narcolepsy type 1. In some embodiments, the cataplexy-like event is cataplexy.

Disclosed herein are methods for treating shift work disorder, shift work sleep disorder or jet lag syndrome in a subject in need thereof, comprising administering to the subject (a) an orexin 2 receptor (OX2R) agonist; and (b) an agent for reducing metabolism of the OX2R agonist.

Further disclosed herein is a combination therapy comprising (a) an orexin 2 receptor (OX2R) agonist; and (b) an agent for reducing metabolism of the OX2R agonist for use in treating shift work disorder, shift work sleep disorder or jet lag syndrome in a subject in need thereof.

Disclosed herein are uses of (a) an orexin 2 receptor (OX2R) agonist; and (b) an agent for reducing metabolism of the OX2R agonist in the manufacture of a medicament for treating shift work disorder, shift work sleep disorder or jet lag syndrome in a subject in need thereof.

In some embodiments, the OX2R agonist is Compound (I).

The methods and uses disclosed herein may treat narcolepsy type 1 in a subject in need thereof. In some embodiments, treating narcolepsy type 1 may comprise reducing or alleviating one or more symptoms of narcolepsy type 1. The one or more symptoms of narcolepsy type 1 may be selected from excessive daytime sleepiness (EDS) and cataplexy. In some embodiments, the one or more symptoms of narcolepsy type 1 is selected from excessive daytime sleepiness (EDS) and cataplexy. Narcolepsy may be diagnosed by diagnostic criteria generally used in the field, e.g., the third edition of the International Classification of Sleep Disorders (ICSD-3) and the fifth edition of the Diagnostic and Statistical Manual of Mental Disorders (DSM-5).

The methods and uses disclosed herein may increase wakefulness and/or decrease and/or treat excessive sleepiness in a subject in need thereof. In some embodiments, wakefulness and/or decrease and/or treatment of excessive sleepiness is determined by electroencephalogram (EEG) and/or electromyogram (EMG). In some embodiments, wakefulness and/or decrease of sleepiness is determined by using the Maintenance Wakefulness Test (MWT). The MWT may be quantified by EEG. An EEG is a test that detects electrical activity in the brain using small, metal discs or electrodes attached to the scalp. In some embodiments, wakefulness and/or decrease of sleepiness is determined by using the multiple sleep latency test (MSLT) or the Oxford Sleep Resistance (OSLER) test. In some embodiments, the test is the Karolinska Sleepiness Scale (KSS), the Epworth Sleepiness Scale (ESS) or the Stanford Sleepiness Scale. In some embodiments, the subject with the excessive sleepiness may suffer from or be diagnosed of narcolepsy type 1, narcolepsy type 2, idiopathic hypersomnia, hypersomnia, hypersomnolence, sleep apnea syndrome (e.g., obstructive sleep apnea, obstructive sleep apnea with use of continuous positive airway pressure); or disturbance of consciousness such as coma and the like; or narcolepsy syndrome accompanied by narcolepsy-like symptoms; hypersomnolence or hypersomnia syndrome accompanied by daytime hypersomnia (e.g., Parkinson's disease, Guillain-barre syndrome and Kleine Levin syndrome); excessive daytime sleepiness in Parkinson's disease, Alzheimer's Disease, DLB (Dementia with Lewy bodies), Prader-Willi Syndrome, depressions (depression, atypical depression, major depressive disorder, treatment resistant depression), Attention Deficit Hyperactivity Disorder (ADHD), sleep apnea syndrome (e.g., obstructive sleep apnea, obstructive sleep apnea with use of continuous positive airway pressure) or other disorders of vigilance; or residual excessive daytime sleepiness in sleep apnea syndrome (e.g., obstructive sleep apnea, obstructive sleep apnea with use of continuous positive airway pressure); or the like. In some embodiments, the excessive sleepiness of the subject may be caused by or associated with narcolepsy type 1, narcolepsy type 2, idiopathic hypersomnia, hypersomnia, hypersomnolence, sleep apnea syndrome (e.g., obstructive sleep apnea, obstructive sleep apnea with use of continuous positive airway pressure), or disturbance of consciousness such as coma and the like; or narcolepsy syndrome accompanied by narcolepsy-like symptoms; hypersomnolence or hypersomnia syndrome accompanied by daytime hypersomnia (e.g., Parkinson's disease, Guillain-barre syndrome and Kleine Levin syndrome), Parkinson's disease, Alzheimer's Disease, DLB (Dementia with Lewy bodies), Prader-Willi Syndrome, depression (depression, atypical depression, major depressive disorder, treatment resistant depression), ADHD, sleep apnea syndrome (e.g., obstructive sleep apnea, obstructive sleep apnea with use of continuous positive airway pressure) or other disorders of vigilance; or the like.

The methods and uses disclosed herein may increase wakefulness and/or decrease and/or treat excessive sleepiness in a subject in need thereof. In some embodiments, the excessive sleepiness is daytime excessive sleepiness.

The methods and uses disclosed herein may increase the plasma concentration of Compound (I), in a subject; or may maintain a pharmaceutically effective plasma concentration of Compound (I) in a subject; or may reduce a time-dependent decrease in the plasma concentration of Compound (I) in a subject. In some embodiments, the plasma concentration of Compound (I) is increased by at least 5-fold, 10-fold, 25-fold, 50-fold, 100-fold, 200-fold, 500-fold, 1000-fold or more upon administration of Compound (I) and an agent for reducing metabolism of Compound (I) wherein the increase is as compared to the plasma concentration of Compound (I) upon administration of Compound (I) alone. In some embodiments, the plasma concentration of Compound (I) in a subject may be measured at least 4, 6, 9, 12, 24, 36, or 48 or more hours after administration of Compound (I) to the subject.

The methods and uses disclosed herein may maintain a pharmaceutically effective plasma concentration of Compound (I) in a subject. In some embodiments, the pharmaceutically effective plasma concentration of Compound (I) may be at least 5, 10, 25, 50, 75, 100, 150, 200, 250, or 300 or more ng/ml. In some embodiments, the pharmaceutically effective plasma concentration of Compound (I) in a subject may be measured at least 4, 6, 9, 12, 24, 36, or 48 or more hours after administration of Compound (I) to the subject.

The methods and uses disclosed herein may increase the Cmax of Compound (I) in a subject. In some embodiments, the Cmax of Compound (I) is increased by at least 5-fold, 10-fold, 25-fold, 50-fold, 100-fold, 200-fold or more upon administration of Compound (I) and an agent for reducing metabolism of Compound (I) wherein the increase is as compared to the Cmax of Compound (I) upon administration of Compound (I) alone.

The methods and uses disclosed herein may increase the AUCinf of Compound (I) in a subject. In some embodiments, the AUCinf of Compound (I) is increased by at least 5-fold, 10-fold, 25-fold, 50-fold, 100-fold, 200-fold, 500-fold or more upon administration of Compound (I) and an agent for reducing metabolism of Compound (I) wherein the increase is as compared to the AUCinf of Compound (I) upon administration of Compound (I) alone.

The methods and uses disclosed herein may increase the AUClast of Compound (I) in a subject. In some embodiments, the AUClast of Compound (I) is increased by at least 5-fold, 10-fold, 25-fold, 50-fold, 100-fold, 200-fold, 500-fold or more upon administration of Compound (I) and an agent for reducing metabolism of Compound (I) wherein the increase is as compared to the AUClast of Compound (I) upon administration of Compound (I) alone.

AUClast and AUCinf may be calculated as follows; AUClast: the area under the concentration-time curve, from time $0$ to the last quantifiable concentration, as calculated by the linear-log trapezoidal method. AUCinf: the area under the concentration-time curve, from time $0$ extrapolated to infinity. $AUC_\infty$ is calculated as AUClast plus the ratio of the last measurable blood concentration to the elimination rate constant.

The methods and uses disclosed herein may decrease cataplexy-like events (e.g., cataplexy) in a subject in need thereof. In some embodiments, the number of cataplexy-like events is decreased by between 1 and 20, or more cataplexy-like events. In some embodiments, the number of cataplexy-like events is decreased by between 1 and 8, or more events in a 24 hour period. In some embodiments, the number of cataplexy-like events is decreased by between 50% and 95%, or more cataplexy-like events, comparing with the case a subject is not administered by Compound (I). In some embodiments, the number of cataplexy-like events is decreased by between 1 and 20, or more events in between a 1-day and 15-day period. The cataplexy-like events include cataplexy.

The methods and uses disclosed herein may treat a disease selected from narcolepsy type 1, narcolepsy type 2, idiopathic hypersomnia, hypersomnia, hypersomnolence, sleep apnea syndrome (e.g., obstructive sleep apnea, obstructive sleep apnea with use of continuous positive airway pressure), and disturbance of consciousness such as coma and the like, and narcolepsy syndrome accompanied by narcolepsy-like symptom, hypersomnolence or hypersomnia syndrome accompanied by daytime hypersomnia (e.g., Parkinson's disease, Guillain-barre syndrome and Kleine Levin syndrome), excessive daytime sleepiness in Parkinson's disease, Alzheimer's Disease, DLB (Dementia with Lewy bodies), Prader-Willi Syndrome, depression (depression, atypical depression, major depressive disorder, treatment resistant depression), ADHD, sleep apnea syndrome (e.g., obstructive sleep apnea, obstructive sleep apnea with use of continuous positive airway pressure), residual excessive daytime sleepiness in sleep apnea syndrome (e.g., obstructive sleep apnea, obstructive sleep apnea with use of continuous positive airway pressure) and other disorders of vigilance, obesity, diabetes, and the like.

The methods and uses disclosed herein may comprise performing one or more tests to quantify a subject's sleepiness. In some embodiments, the test is selected from MSLT, MWT, and OSLER test. In some embodiments, the test is MWT. In some embodiments, the test is KSS, ESS or the Stanford Sleepiness Scale.

The methods and uses disclosed herein comprise administering Compound (I) to a subject in need thereof. In some embodiments, Compound (I) is administered orally. In some embodiments, Compound (I) is administered non-orally. In some embodiments, the non-oral administration is intravenous administration, subcutaneous administration, transdermal administration, intradermal administration or transmucosal administration.

Compound (I) can be administered orally and non-orally, such as intramuscular, intraperitoneal, intravenous, intraarterial, intraventricular, intracisternal injection or infusion; subcutaneous injection; or implant; or inhalation spray, intratracheal, nasal, vaginal, rectal, subdermal, transdermal, intradermal, epidural, ocular insert or ocular instillation administration, in a suitable unit dosage form containing a pharmaceutically acceptable conventional nontoxic carrier, adjuvant and vehicle suitable for each administration route.

Alternatively, or additionally, administering Compound (I) may comprise administering an effective amount of Compound (I). In some embodiments, administering Compound (I) may comprise administering a therapeutically effective amount of Compound (I). The effective amount of Compound (I) may be between about 3 mg to about 500 mg. The effective amount of Compound (I) may be between about 3 mg to about 400 mg. The effective amount of Compound (I) may be between about 3 mg to about 300 mg. The effective amount of Compound (I) may be between about 3 mg to about 200 mg. The effective amount of Compound (I) may be between about 3 mg to 100 mg. The effective amount of Compound (I) may be between about 3 mg to 50 mg. In some embodiments, the effective amount and therapeutically effective amount may be the same. The effective amount of Compound (I) may be between 5 and 300 mg. The effective amount of Compound (I) may be between 5 and 250 mg. The effective amount of Compound (I) may be between 5 and 200 mg. The effective amount of Compound (I) may be between 5 and 150 mg. The effective amount of Compound (I) may be between 5 and 100 mg. The effective amount of Compound (I), or a salt thereof, may be between 5 and 50 mg. The effective amount of Compound (I) may be between 10 and 300 mg. The effective amount of Compound (I) may be between 10 and 250 mg. The effective amount of Compound (I) may be between 10 and 200 mg. The effective amount of Compound (I) may be between 10 and 150 mg. The effective amount of Compound (I) may be between 10 and 100 mg. The effective amount of Compound (I) may be between 10 and 50 mg. In some embodiments, the effective amount and therapeutically effective amount are the same.

Compound (I) may be administered between 1 and 3, or more times per day. In some embodiments, Compound (I) is administered at least once per day. In some embodiments, Compound (I) is administered at least twice per day.

Compound (I) may be administered between 1 and 7, or more times per week. In some embodiments, Compound (I)

is administered at once per week. In some embodiments, Compound (I) is administered at least twice per week. In some embodiments, Compound (I) is administered at least 3 times per week.

The compositions, methods, and uses disclosed herein may comprise an agent for reducing metabolism of an OX2R agonist. The agent for reducing metabolism of the OX2R agonist may increase bioavailability of the OX2R agonist or systemic exposure of the OX2R agonist. The agent for reducing metabolism of the OX2R agonist may reduce 1st pass metabolism or systemic clearance of the OX2R agonist. The agent for reducing metabolism of the OX2R agonist may enhance the pharmacokinetics of the OX2R agonist. The agent for reducing metabolism of the OX2R agonist may increase the plasma concentration of the OX2R agonist. In some embodiments, the OX2R agonist is Compound (I). In some embodiments, Compound (I) is methyl (2R,3S)-3-((methylsulfonyl)amino)-2-(((cis-4-phenylcyclohexyl)oxy)methyl) piperidine-1-carboxylate (hereafter "Compound A") or a salt thereof. In some embodiments, the agent for reducing metabolism of the OX2R agonist is an inhibitor of one or more enzymes of the Cytochrome P450 enzyme system. In some embodiments, the agent for reducing metabolism of the OX2R agonist is a CYP3A inhibitor. In some embodiments, the agent for reducing metabolism of the OX2R agonist is a CYP3A4 inhibitor. In some embodiments, the CYP3A4 inhibitor is selected from the group consisting of atazanavir, boceprevir, clarithromycin, cobicistat, conivaptan, curcumin, danazol, danoprevir, darunavir, delavirdine, diltiazem, ditiocarb, econazole, efavirenz, elvitegravir, ergotamine, idelalisib, indinavir, itraconazole, ketoconazole, loperamide, lopinavir, methimazole, midostaurin, naloxone, nefazodone, nelfinavir, nilotinib, posaconazole, ribociclib, ritonavir, saquinavir, stiripentol, telaprevir, telithromycin, terfenadine, tipranavir, troleandomycin, and voriconazole. In some embodiments, the CYP3A4 inhibitor is selected from the group consisting of ritonavir and cobicistat. In some embodiments, the CYP3A4 inhibitor is cobicistat.

The agent for reducing metabolism of an OX2R agonist may be administered simultaneously with Compound (I). The agent for reducing metabolism of an OX2R agonist may be administered after administration of an OX2R agonist. The agent for reducing metabolism of an OX2R agonist may be administered prior to administration of an OX2R agonist. In some embodiments, the agent for reducing metabolism of an OX2R agonist is administered daily (a single daily dose or multiple daily doses). In some embodiments, the agent for reducing metabolism of an OX2R agonist is administered once per day. In some embodiments, the agent for reducing metabolism of an OX2R agonist is administered at least twice per day.

The agent for reducing metabolism of an OX2R agonist may be administered orally and non-orally, such as intramuscular, intraperitoneal, intravenous, intraarterial, intraventricular, intracisternal injection or infusion; subcutaneous injection; or implant; or inhalation spray, intratracheal, nasal, vaginal, rectal, subdermal, transdermal, intradermal, epidural, ocular insert or ocular instillation administration, in a suitable unit dosage form containing a pharmaceutically acceptable conventional nontoxic carrier, adjuvant and vehicle suitable for each administration route. The agent for reducing metabolism of an OX2R agonist may be administered orally.

The agent for reducing metabolism of an OX2R agonist may be formulated with an OX2R agonist. The agent for reducing metabolism of an OX2R agonist may be formulated separately from an OX2R agonist. The compositions or combination therapies disclosed herein may comprise a single container that comprises an OX2R agonist and the agent for reducing metabolism of an OX2R agonist. Alternatively, the compositions or combination therapies disclosed herein may comprise a first container that comprises an OX2R agonist and a second container that comprises the agent for reducing metabolism of an OX2R agonist.

The agent for reducing metabolism of an OX2R agonist may be administered between 1 and 3, or more times per day. In some embodiments, the agent for reducing metabolism of an OX2R agonist is administered at least once per day. In some embodiments, the agent for reducing metabolism of an OX2R agonist is administered at least twice per day.

The agent for reducing metabolism of an OX2R agonist may be administered between 1 and 7, or more times per week. In some embodiments, the agent for reducing metabolism of an OX2R agonist is administered at once per week. In some embodiments, the agent for reducing metabolism of an OX2R agonist is administered at least twice per week. In some embodiments, the agent for reducing metabolism of an OX2R agonist is administered at least 3 times per week.

The agent for reducing metabolism of an OX2R agonist may be cobicistat. Administering cobicistat may comprise administering an effective amount of cobicistat. In some embodiments, administering cobicistat may comprise administering a therapeutically effective amount of cobicistat. The effective amount of cobicistat may be between 5 mg and 500 mg, 10 mg and 400 mg, 50 mg and 300 mg, 75 mg and 250 mg, or 100 mg and 200 mg. In some embodiments, the effective amount of cobicistat may be 150 mg.

The agent for reducing metabolism of an OX2R agonist may be ritonavir. Administering ritonavir may comprise administering an effective amount of ritonavir. In some embodiments, administering ritonavir may comprise administering a therapeutically effective amount of ritonavir. The effective amount of ritonavir may be between 5 mg and 500 mg, 10 mg and 400 mg, 15 mg and 300 mg, 20 mg and 200 mg, or 25 mg and 100 mg. In some embodiments, the effective amount of ritonavir may be 25 mg, 50 mg or 100 mg.

The compositions, methods, and uses disclosed herein may comprise an agent for reducing metabolism of Compound (I). The agent for reducing metabolism of Compound (I) may increase bioavailability of Compound (I) or systemic exposure of Compound (I). The agent for reducing metabolism of Compound (I) may reduce $1^{st}$ pass metabolism or systemic clearance of Compound (I). The agent for reducing metabolism of Compound (I) may enhance the pharmacokinetics of Compound (I). The agent for reducing metabolism of Compound (I) may increase the plasma concentration of Compound (I). In some embodiments, the agent for reducing metabolism of Compound (I) is an inhibitor of one or more enzymes of the Cytochrome P450 enzyme system. In some embodiments, the agent for reducing metabolism of Compound (I) is a CYP3A inhibitor. In some embodiments, the agent for reducing metabolism of Compound (I) is a CYP3A4 inhibitor. In some embodiments, the CYP3A4 inhibitor is selected from the group consisting of atazanavir, boceprevir, clarithromycin, cobicistat, conivaptan, curcumin, danazol, danoprevir, darunavir, delavirdine, diltiazem, ditiocarb, econazole, efavirenz, elvitegravir, ergotamine, idelalisib, indinavir, itraconazole, ketoconazole, loperamide, lopinavir, methimazole, midostaurin, naloxone, nefazodone, nelfinavir, nilotinib, posaconazole, ribociclib, ritonavir, saquinavir, stiripentol, telaprevir, telithromycin, terfenadine, tipranavir, troleandomycin, and voriconazole. In some embodiments, the CYP3A4 inhibitor is selected from the group consisting of ritonavir and cobicistat. In some embodiments, the CYP3A4 inhibitor is cobicistat.

The agent for reducing metabolism of Compound (I) may be administered simultaneously with Compound (I). The agent for reducing metabolism of Compound (I) may be administered after administration of Compound (I). The agent for reducing metabolism of Compound (I) may be administered prior to administration of Compound (I). In some embodiments, the agent for reducing metabolism of Compound (I) is administered daily (a single daily dose or multiple daily doses). In some embodiments, the agent for reducing metabolism of Compound (I) is administered once per day. In some embodiments, the agent for reducing metabolism of Compound (I) is administered at least twice per day.

The agent for reducing metabolism of Compound (I) may be administered orally and non-orally, such as intramuscular, intraperitoneal, intravenous, intraarterial, intraventricular, intracisternal injection or infusion; subcutaneous injection; or implant; or inhalation spray, intratracheal, nasal, vaginal, rectal, subdermal, transdermal, intradermal, epidural, ocular insert or ocular instillation administration, in a suitable unit dosage form containing a pharmaceutically acceptable conventional nontoxic carrier, adjuvant and vehicle suitable for each administration route. The agent for reducing metabolism of Compound (I) may be administered orally.

The agent for reducing metabolism of Compound (I) may be formulated with Compound (I). The agent for reducing metabolism of Compound (I) may be formulated separately from Compound (I). The compositions or combination therapies disclosed herein may comprise a single container that comprises Compound (I) and the agent for reducing metabolism of Compound (I). Alternatively, the compositions or combination therapies disclosed herein may comprise a first container that comprises Compound (I) and a second container that comprises the agent for reducing metabolism of Compound (I).

The agent for reducing metabolism of Compound (I) may be administered between 1 and 3, or more times per day. In some embodiments, the agent for reducing metabolism of Compound (I) is administered at least once per day. In some embodiments, the agent for reducing metabolism of Compound (I) is administered at least twice per day.

The agent for reducing metabolism of Compound (I) may be administered between 1 and 7, or more times per week. In some embodiments, the agent for reducing metabolism of Compound (I) is administered at once per week. In some embodiments, the agent for reducing metabolism of Compound (I) is administered at least twice per week. In some embodiments, the agent for reducing metabolism of Compound (I) is administered at least 3 times per week.

The agent for reducing metabolism of Compound (I) may be cobicistat. Administering cobicistat may comprise administering an effective amount of cobicistat. In some embodiments, administering cobicistat may comprise administering a therapeutically effective amount of cobicistat. The effective amount of cobicistat may be between 5 mg and 500 mg, 10 mg and 400 mg, 50 mg and 300 mg, 75 mg and 250 mg, or 100 mg and 200 mg. In some embodiments, the effective amount of cobicistat may be 150 mg.

The agent for reducing metabolism of Compound (I) may be ritonavir. Administering ritonavir may comprise administering an effective amount of ritonavir. In some embodiments, administering ritonavir may comprise administering a therapeutically effective amount of ritonavir. The effective amount of ritonavir may be between 5 mg and 500 mg, 10 mg and 400 mg, 15 mg and 300 mg, 20 mg and 200 mg, or 25 mg and 100 mg. In some embodiments, the effective amount of ritonavir may be 25 mg, 50 mg or 100 mg.

The methods disclosed herein may further comprise administering one or more additional therapies. The kits and compositions disclosed herein may further comprise one or more additional therapies. The one or more additional therapies may be selected from stimulant, antidepressant, central nervous system depressant, histamine 3 (H3) receptor antagonist, and any other concomitant drugs described herein. In some embodiments, the stimulant is modafinil. In some embodiments, the antidepressant is clomipramine. In some embodiments, the central nervous system depressant is sodium oxybate. In some embodiments, the H3 receptor antagonist is pitolisant.

Two or more kinds of the above-mentioned concomitant drug may be used in a mixture at an appropriate ratio.

The methods disclosed herein may not further comprise administering one or more additional agent for reducing metabolism of Compound (I). The kits and compositions disclosed herein may not further comprise one or more additional agent for reducing metabolism of Compound (I).

Further disclosed herein are pharmaceutical compositions comprising (a) methyl 3-((methylsulfonyl)amino)-2-(((4-phenylcyclohexyl)oxy)methyl) piperidine-1-carboxylate (Compound (I)), or a salt thereof; (b) an agent for reducing metabolism of Compound (I); and (c) a pharmaceutically acceptable carrier therefor.

Further disclosed herein are pharmaceutical compositions comprising (a) an OX2R agonist; (b) an agent for reducing metabolism of the OX2R agonist; and (c) a pharmaceutically acceptable carrier therefor.

The pharmaceutically acceptable carrier may be a cyclodextrin. The cyclodextrin may be betadex sulfobutyl ether sodium.

In some embodiments, various organic or inorganic carrier substances conventionally used as preparation materials are used as a pharmaceutically acceptable carrier. These are incorporated as excipient, lubricant, binder and disintegrant for solid preparations; or solvent, solubilizing agent, suspending agent, isotonicity agent, buffer and soothing agent for liquid preparations; and the like; and preparation additives such as preservative, antioxidant, colorant, sweetening agent and the like can be added as necessary.

Examples of the dosage form of the aforementioned pharmaceutical composition include tablet (including sugar-coated tablet, film-coated tablet, orally disintegrating tablet), capsule (including soft capsule, microcapsule), granule, powder, troche, syrup, emulsion, suspension, films (e.g., orally disintegrable films), injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparation, pulmonary preparation (inhalant), eye drop and the like, which can be respectively safely administered orally or non-orally (e.g., topical, rectal, intravenous administration). These preparations may be a release control preparation (e.g., sustained-release microcapsule) such as an immediate-release preparation, a sustained-release preparation and the like.

In some embodiments, the pharmaceutical composition is formulated for oral administration. In some embodiments, the pharmaceutical composition is formulated for non-oral administration. In some embodiments, the pharmaceutical composition is formulated for intravenous administration, subcutaneous administration, transdermal administration, intradermal administration or transmucosal administration. In some embodiments, the pharmaceutical composition is formulated for intravenous administration. In some embodiments, the pharmaceutical composition is formulated for subcutaneous administration. In some embodiments, the pharmaceutical composition is formulated for transdermal administration.

In some embodiments, the OX2R agonist is Compound (I). In some embodiments, Compound (I) is an optically active compound. In some embodiments, Compound (I) is methyl (2R,3S)-3-((methylsulfonyl)amino)-2-(((cis-4-phenylcyclohexyl)oxy)methyl) piperidine-1-carboxylate (Compound A). Compound (I) (including its optically active compound) may be produced as disclosed in WO2017/135306, which is incorporated by reference in its entirety.

Further disclosed herein are kits comprising Compound (I). In some embodiments, the kit comprises (a) a container comprising Compound (I); (b) a container comprising an agent for reducing metabolism of Compound (I); and (c) instructions for administering Compound (I) and the agent.

Further disclosed herein are kits comprising an OX2R agonist. In some embodiments, the kit comprises (a) an OX2R agonist; (b) a container comprising an agent for reducing metabolism of the OX2R agonist; and (c) instructions for administering (a) and (b).

The kits disclosed herein may further comprise an additional container comprising saline.

The container may be a glass vial. Alternatively, the container may be a syringe.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the singular forms "a", "an" and "the" are intended to include the plural forms as well, unless the context clearly indicates otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "administration" of an agent to a subject includes any route of introducing or delivering the agent to a subject to perform its intended function. Administration can be carried out by oral route or any suitable non-oral route, including, but not limited to, intravenously, intramuscularly, intraperitoneally, subcutaneously, and other suitable routes as described herein. Administration includes self-administration and the administration by another.

As used herein, the term "effective amount" or "therapeutically effective amount" refers to a quantity of Compound (I) (or OX2R agonist) sufficient to achieve a desired effect or a desired therapeutic effect. In the context of therapeutic applications, the amount of Compound (I) (or OX2R agonist) administered to the subject can depend on the type and severity of the disease (e.g., narcolepsy, narcolepsy type 1) or symptom and on the characteristics of the individual, such as general health, age, sex, body weight and tolerance to drugs. The skilled artisan will be able to determine appropriate dosages depending on these and other factors.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "an OX2R agonist" refers to an orexin neuropeptide agonist that acts on the orexin 2 receptor. In some embodiments, the OX2R agonist is Compound (I). In some embodiments, Compound (I) is methyl (2R,3S)-3-((methylsulfonyl)amino)-2-(((cis-4-phenylcyclohexyl)oxy)methyl) piperidine-1-carboxylate (hereafter "Compound A") or a salt thereof.

EXAMPLES

The following examples are put forth so as to provide those of ordinary skill in the art with a complete disclosure and description of how to make and use the compositions, and assay, screening, and therapeutic methods of the invention, and are not intended to limit the scope of what the inventors regard as their invention.

Example 1: a Phase 1, Open-Label Study to Evaluate the Effects of Cobicistat on the Single Dose Pharmacokinetics of Compound a Administered Orally to Healthy Subjects The purpose of this study was to evaluate the effect of cobicistat on Compound A. The primary goal was to evaluate whether cobicistat can boost plasma concentrations of oral Compound A in humans and therefore, can be used in combination with Compound A as part of an oral dose regimen. The magnitude of this intentional drug-drug interaction (DDI) is also quantified.

The other aim of this study was to assess the time course of CYP3A inactivation by cobicistat, to characterize the onset of CYP3A inhibition and attainment of steady-state levels of inhibition. Midazolam is a benzodiazepine derivative that is exclusively metabolized by the CYP3A enzymatic pathway and therefore, was used as an in vivo probe for human CYP3A activity.

Study Objective(s)

1. Primary Objective:
   To evaluate the effect of steady-state cobicistat on the single-dose pharmacokinetics of Compound A administered orally 2. Secondary Objective:
   To evaluate the safety and tolerability of a single oral dose of Compound A with and without cobicistat.

Study Endpoints

1. Primary Endpoints
   Plasma PK parameters of Compound A ($AUC_\infty$, $AUC_{last}$, $C_{max}$) after oral administration with and without cobicistat 2. Secondary Endpoints
   Adverse events Brief Overview of Study Design This was a non-randomized, open-label, fixed-sequence study in healthy male and female (women of non-childbearing potential [WONCBP]) subjects.

On Day 1, subjects received 1 mg midazolam orally and pharmacokinetic (PK) blood samples for midazolam (and its metabolite 1-hydroxy (1-OH) midazolam) were collected predose and up until 24 hours postdose to establish baseline cytochrome P450 (CYP) 3A activity. On Day 2, subjects received 14 mg Compound A over a 9-hour intravenous (IV) infusion and PK blood samples for Compound A were collected predose and up until 15 hours after end of infusion. On Day 3, subjects received 112 mg Compound A orally and PK blood and urine samples for Compound A were collected predose and up until 48 hours postdose.

On Days 5 through 13, subjects received 150 mg cobicistat orally once daily (QD), and PK blood samples for cobicistat were collected predose on Day 5 and up until 24 hours postdose. Predose blood samples for cobicistat PK were also collected on Days 7, 9, 10, and 11.

On Days 7 and 10, 0.5 mg midazolam were administered orally (30 minutes after the cobicistat dose) and PK blood for midazolam and 1-OH midazolam were collected on each of these days, predose and up until 24 hours post midazolam dosing.

On Day 12, 14 mg Compound A were administered orally (30 minutes after the cobicistat dose) and PK blood and urine samples for Compound A were collected predose and up until 48 hours post Compound A dosing; PK blood samples for cobicistat were collected predose on Day 12 and up until 24 hours post cobicistat dosing and at 24-hour post Day 13 cobicistat dosing.

Safety was assessed by monitoring for adverse events (AEs), vital signs, safety 12-lead electrocardiograms (ECGs), safety laboratory assessments, pulse oximetry, C-SSRS (Columbia Suicide Severity Rating Scale), and physical examinations throughout the study.

A summary of the overall study design is depicted in FIG. 1.

TABLE 1

Summary of Pharmacokinetics and Safety Assessment Timing for Days 1 to 14 Inclusively

| Day Procedures | 1 | 1 | 2 | 2 | 2 (Compound A IV infusion) | 3 | 3 (Compound A Oral dosing) | 4 | 5 | 5 | 6 | 6 | 7 | 7 | 7 |
|---|---|---|---|---|---|---|---|---|---|---|---|---|---|---|---|
| | Predose | MDZ dosing | MDZ dosing | Predose | A IV infusion | Predose | Compound A Oral dosing | | Predose | COBI dosing | Predose | COBI dosing | Predose | COBI dosing | MDZ dosing |
| Blood sample for MDZ and 1-OH MDZ PK | Pre MDZ dosing | 0.5, 1, 1.5, 2, 4, 6, 8, 12 h postdose | 24 h post MDZ dosing | | | | | | | | | | Pre COBI and MDZ dosing | | 0.5, 1, 1.5, 2, 4, 6, 8, 12 h post MDZ dosing |
| Blood sample for Compound A PK after IV infusion | | | | Pre Compound A dosing | 1, 2, 4, 9, 9, 17, 10, 13 h post start of IV infusion | 24 h post start of IV infusion | | | | | | | | | |
| Blood sample for Compound A PK after oral dosing | | | | | | Pre Compound A dosing | 0.17, 0.33, 0.5, 1, 2, 4, 6, 9, 12 h post Compound A oral dosing | 24, 36 h post Compound A oral dosing | 48 h post Compound A oral dosing | | | | | | |
| Urine sample for Compound A PK after oral dosing | | | | | | Spot: Pre Compound A dosing | Pooled: 0-6, and 6-12 h post Compound A oral dosing | Pooled: 12-24 h Post Compound A oral dosing | Pooled: 24-48 h Post Compound A oral dosing | | | | | | |
| Blood sample for cobicistat PK | | | | | | | | | Pre COBI dosing | 0.5, 1, 2, 4, 6, 9, 12 h post COBI dosing | 24 h post COBI dosing | | Pre COBI and MDZ dosing | | |

| Day Procedures | 8 | 8 | 9 | 9 | 10 | 10 | 11 | 11 | 12 (Compound) | 12 | 12 | 13 | 13 | 14 |
|---|---|---|---|---|---|---|---|---|---|---|---|---|---|---|
| | Predose | COBI dosing | Predose | COBI dosing | Predose | COBI dosing | Predose | MDZ dosing | Predose | COBI dosing | Compound A oral dosing | Predose | COBI dosing | DC/ET |
| Blood sample for MDZ and 1-OH MDZ PK | 24 h post MDZ dosing | | | | Pre COBI and MDZ dosing | | 24 h post MDZ dosing | 0.5, 1, 1.5, 2, 4, 6, 8, 12 h post MDZ dosing | | | | | | |
| Blood sample for Compound A PK after oral dosing | | | | | | | | | Pre COBI and Compound A dosing | | 0.17, 0.33, 0.5, 1, 2, 4, 6, 9, 12 h post Compound A oral dosing | 24 h post Compound A oral dosing | 36 h post Compound A oral dosing | 48 h post Compound A oral dosing |

TABLE 1-continued

Summary of Pharmacokinetics and Safety Assessment Timing for Days 1 to 14 Inclusively

| | | | | | |
|---|---|---|---|---|---|
| Urine sample for Compound A PK after oral dosing | | | Urine spot Pre COBI and Compound A dosing | Pooled: 0-6, 6-12 h post Compound A oral dosing | Pooled: 12-24 h post Compound A oral dosing | Pooled: 24-48 h post Compound A oral dosing |
| Blood sample for cobicistat PK | Pre COBI dosing | Pre COBI and MDZ dosing | Pre COBI dosing | Pre COBI dosing | Pre COBI 0.5, 1, 2, 4, and 6, 9, 12 h Compound post COBI A dosing dosing | 24 h post COBI dosing | 24 h post Day 13 COBI dosing |

Abbreviations:
1-OH MDZ= 1-hydroxy midazolam,
BP = Blood pressure,
COBI = cobicistat,
DC = discharge,
ECG = Electrocardiogram,
ET = Early Termination,
h = hour,
IV= intravenous,
MDZ = Midazolam,
PK = Pharmacokinetics,
Pre = Predose.

Study Subject Population

Healthy male and female subjects aged 19 to 55 years inclusive, at screening. Body Mass Index (BMI) 18.0-32.0 kg/m², inclusive, at screening.

Key Inclusion Criteria:

Healthy, adult, male or female (of non-childbearing potential) 19-55 years of age, inclusive, at screening.

Continuous non-smoker who has not used nicotine containing products for at least 90 days prior to the first dosing and throughout the study.

Body mass index (BMI)≥18.0 and ≤32.0 kg/m² at screening, inclusive.

Medically healthy with no clinically significant medical history, physical examination, laboratory profiles, vital signs, or ECGs, as deemed by the investigator or designee.

Key Exclusion Criteria:

Was mentally or legally incapacitated or had significant emotional problems at the time of the screening visit or expected during the conduct of the study.

History or presence of clinically significant medical or psychiatric condition or disease in the opinion of the investigator or designee.

History of any illness that, in the opinion of the investigator or designee, might have confound the results of the study or posed an additional risk to the subject by their participation in the study.

History or presence of alcoholism or drug abuse within the past 2 years prior to the first dosing per the Diagnostic and Statistical Manual of Mental Disorders-V criteria.

Unable to refrain from or anticipates the use of:

Any drugs known to be significant inducers or inhibitor of CYP3A4 enzymes and/or P-gp, including St. John's Wort, within 28 days prior to the first dosing, throughout the study and until the follow-up visit. Appropriate sources (e.g., Flockhart Table™) were consulted to confirm lack of PK/pharmacodynamics interaction with the study drug(s).

Any drug, including prescription and non-prescription medications, herbal remedies, antacids or vitamin supplements within 28 days prior to the first dosing and throughout the study and until the follow-up visit. The product label was consulted to confirm there are no severe drug interactions [TYBOST® 2018]. After the first dosing, acetaminophen (up to 2 g per 24 hours) may have been administered at the discretion of the Investigator or designee. Thyroid hormone replacement medication may have been permitted if the subject had been on the same stable dose for the immediate 3 months prior to the first dosing.

Main Criteria for Evaluation and Analyses

The primary endpoints of the study:

Plasma pharmacokinetic parameters of Compound A after oral administration with and without cobicistat as follows Maximum observed concentration (Cmax).

Area under the concentration-time curve from time 0 to infinity, calculated using the observed value of the last quantifiable concentration (AUCinf).

Area under the concentration-time curve from time 0 to the time of the last quantifiable concentration (AUClast).

Blood PK Sampling for Compound A:

Study Day 2: predose (prior to start of Compound A IV infusion), 1, 2, 4, 9, 9.17, 10 and 13 hours after start of infusion Study Day 3:24 hours post Day 2 dosing (predose (prior to Compound A oral administration)) and 0.17, 0.33, 0.5, 1, 2, 4, 6, 9 and 12 hours postdose Study Day 4:24 and 36 hours post Day 3 dosing Study Day 5:48 hours post Day 3 dosing and prior to cobicistat administration Study Day 12-14: predose (prior to cobicistat and Compound A oral administration) and 0.17, 0.33, 0.5, 1, 2, 4, 6, 9, 12, 24, 36 and 48 hours post Compound A oral dosing Blood PK Sampling for Cobicistat:

Study Day 5: predose (prior to cobicistat administration) and 0.5, 1, 2, 4, 6, 9 and 12 hours postdose Study Day 6:24 hours post Day 5 dosing and prior to cobicistat administration Study Day 7: predose (prior to cobicistat and midazolam administration)

Study Day 9: predose (prior to cobicistat administration)

Study Day 10: predose (prior to cobicistat and midazolam administration)

Study Day 11: predose (prior to cobicistat administration)

Study Day 12: predose (prior to cobicistat and Compound A oral administration) and 0.5, 1, 2, 4, 6, 9 and 12 hours post cobicistat dosing Study Day 13:24 hours post Day 12 dosing and prior to cobicistat administration Study Day 14:24 hours post Day 13 dosing Blood PK Sampling for Midazolam and its Metabolite (1-Hydroxymidazolam):

Study Day 1: predose (prior to midazolam administration), 0.5, 1, 1.5, 2, 4, 6, 8, 12 hours postdose Study Day 2:24 hours post Day 1 dosing and prior to start of Compound A IV infusion Study Day 7: predose (prior to cobicistat and midazolam administration), 0.5, 1, 1.5, 2, 4, 6, 8, 12 hours post midazolam dosing Study Day 8:24 hours post Day 7 midazolam dosing and prior to cobicistat administration Study Day 10: predose (prior to cobicistat and midazolam administration), 0.5, 1, 1.5, 2, 4, 6, 8, 12 hours post midazolam dosing Study Day 11:24 hours post Day 10 midazolam dosing and prior to cobicistat administration PK Parameter Analysis:

Plasma pharmacokinetic parameters of Compound A after oral administration with and without cobicistat (Cmax, AUCinf and AUClast) were calculated.

A summary of statistical comparisons of dose-normalized plasma Compound A PK following 112 mg Compound A Oral Alone on Day 3 and 14 mg Compound A Oral+MD 150 mg Cobicistat on Day 12 in healthy subjects is presented in Table 2.

TABLE 2

Summary Statistics of Dose-Normalized Plasma Compound A Pharmacokinetics Following a Single Oral Dose of 112
mg Compound A Alone on Day 3 and a Single Oral Dose of 14 mg Compound A on Day 12
Coadministered With Multiple Once-Daily Oral Doses of 150 mg Cobicistat on Days 5-13 in Healthy Subjects
Dose-Normalized Plasma Compound A Pharmacokinetic Parameter Treatment Ratios Following Administration of a Single Oral Dose
of 14 mg Compound A on Day 12 Coadministered With Multiple Once-Daily Oral Doses of 150 mg Cobicistat on Days 5-13
Versus Following a Single Oral Dose of 112 mg Compound A Alone on Day 3 in Healthy Subjects

| Subject | DNCmax112 (Day 12) (ng/ml/112 mg Compound A) | DNCmax112 (Day 3) (ng/ml/112 mg Compound A) | DNCmax 112Ratio (Day 12/Day 3) (%) | DNAUCinfl112 (Day 12) (ng*hr/mL/112 mg Compound A) | DNAUCinfl112 (Day 3) (ng*hr/mL/112 mg Compound A) | DNAUCI nf 112Ratio (Day 12/Day 3) (%) | DNAUClast112 (Day 12) (ng*hr/mL/112 mg Compound A) | DNAUClast112 (Day 3) (ng*hr/mL/112 mg Compound A) | DNAUClast 112Ratio (Day 12/Day 3) (%) |
|---|---|---|---|---|---|---|---|---|---|
| n | 15 | 15 | 15 | 15 | 15 | 15 | 15 | 15 | 15 |
| Mean | 2335 | 66.35 | 8290 | 8448 | 94.59 | 14349 | 8231 | 94,21 | 14385 |
| SD | 680.74 | 59.780 | 11290 | 4626.8 | 74.402 | 11479 | 4183.3 | 74.495 | 11888 |
| CV % | 29.1 | 90.1 | 136.2 | 54,8 | 78.7 | 80.0 | 508 | 79.1 | 82.6 |
| Geom Mean | 2253 | 44.81 | 5028 | 7623 | 69.67 | 10942 | 7504 | 69.02 | 10871 |
| Geom CV % | 27.7 | 135.8 | 120.6 | 46.6 | 105.3 | 89.7 | 44.5 | 107.0 | 909 |

Day 3 = 112 mg Compound A Oral Alone
Day 12 = 14 mg Compound A Oral + MD 150 mg Cobicistat
Note:
Actual sampling times were used for pharmacokinetic parameter calculations.

The results showed that the dose-normalized Cmax, AUCinf, and AUClast of plasma Compound A were much higher following 14 mg Compound A Oral+MD 150 mg Cobicistat on Day 12 than following 112 mg Compound A Oral Alone on Day 3.

Figure 2:
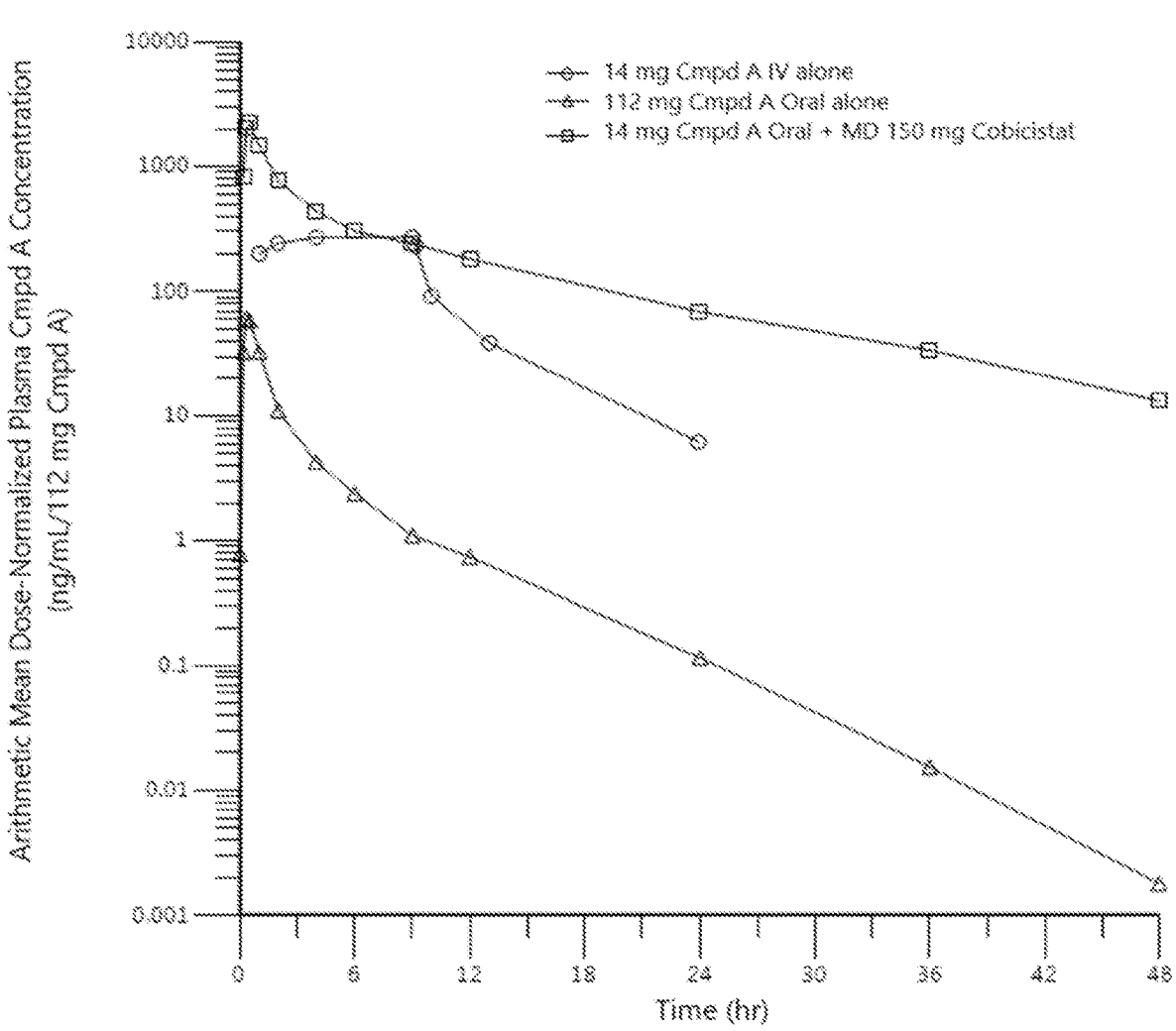
FIG. 2 shows a graph of the Arithmetic Mean Dose-Normalized (to a 112 mg Compound A Dose) Plasma Compound A Concentrations versus Time following a single dose of 14 mg of Compound A alone administered intravenously over 9 hours on Day 2, a single oral dose of 112 mg of Compound A alone on Day 3, and a single oral dose of 14 mg of Compound A on Day 12 co-administered with multiple once-daily oral doses of 150 mg cobicistat on Days 5-13 in healthy subjects.
Figure 3:
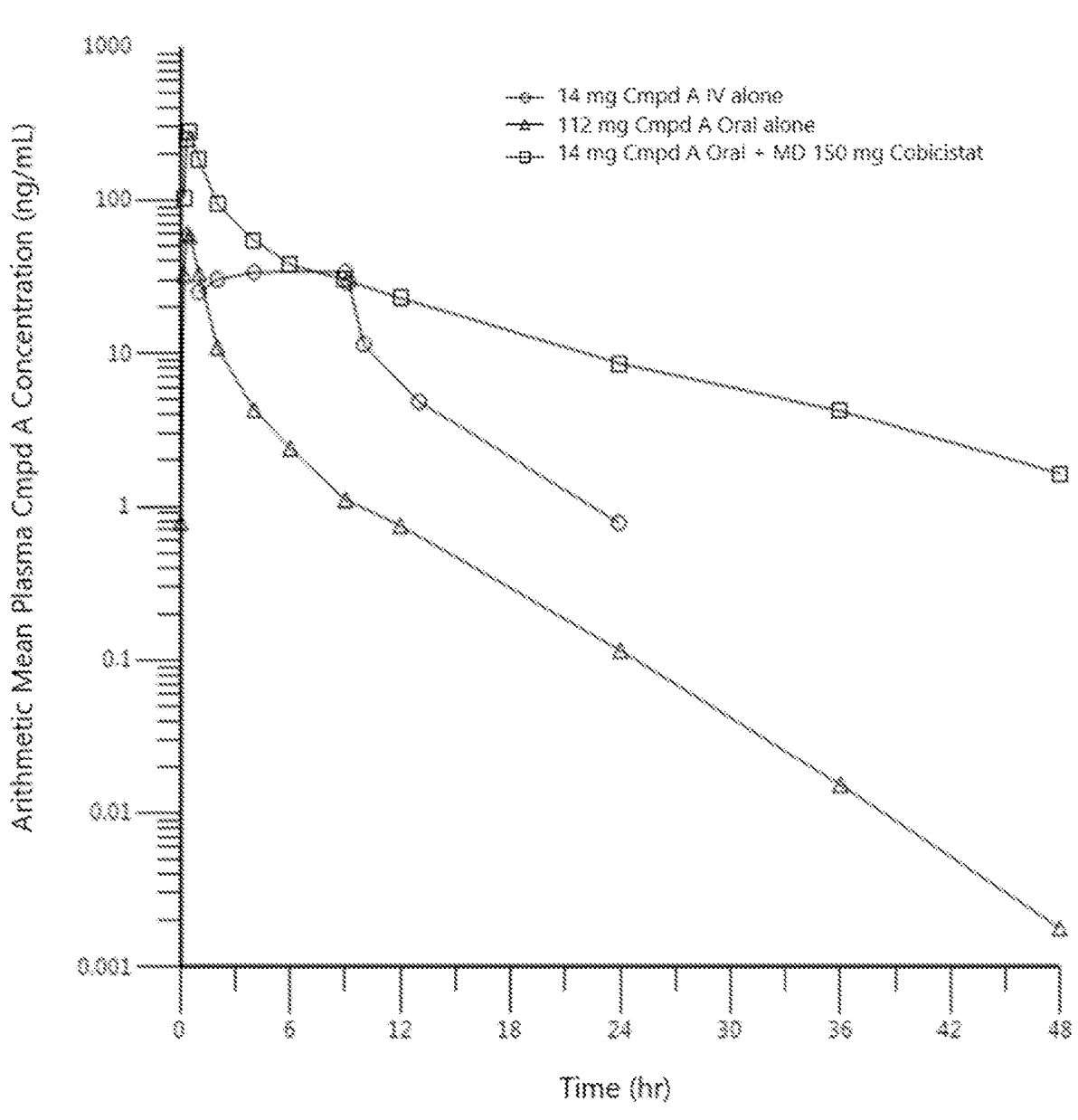
FIG. 3 shows the Arithmetic Mean Plasma Compound A Concentrations versus Time following a single dose of 14 mg of Compound A alone administered intravenously over 9 hours on Day 2, a single oral dose of 112 mg of Compound A alone on Day 3, and a single oral dose of 14 mg of Compound A on Day 12 co-administered with multiple once-daily oral doses of 150 mg cobicistat on Days 5-13 in healthy subjects.

Arithmetic mean plasma concentration-time profiles of Compound A following 14 mg Compound A IV alone on Day 2, 112 mg Compound A Oral alone on Day 3, and 14 mg Compound A Oral+MD 150 mg Cobicistat on Day 12 in healthy subjects are presented in semi-log scale normalized to a Compound A dose of 112 mg in FIG. 2 and non-normalized in FIG. 3, respectively.

Pharmacokinetic Results

Plasma Compound A

After being dose-normalized to 112 mg, coadministration of 14 mg Compound A Oral+QD 150 mg Cobicistat increased the geometric LSM (least-squares mean) Cmax and AUCs (AUClast and AUC∞) of Compound A by approximately 50-fold and 109-fold, respectively, of the corresponding values following 112 mg Compound A Oral Alone.

The geometric mean dose-normalized Cmax and AUC∞ of Compound A were approximately 84% and 97% lower, respectively, following 112 mg Compound A Oral Alone compared to 14 mg Compound A IV Alone, respectively.

The geometric mean dose-normalized Cmax and AUC∞ of Compound A increased by 7.9- and 2.8-fold, respectively, following 14 mg Compound A Oral+QD 150 mg Cobicistat compared to 14 mg Compound A IV Alone (9-hour IV infusion), respectively.

Coadministration of 14 mg Compound A Oral+QD 150 mg Cobicistat prolonged the mean $t_{1/2z}$ of Compound A to ~8 hours compared to 4.9 hours following 112 mg Compound A Oral Alone and 3.7 hours following 14 mg Compound A IV Alone.

Plasma Midazolam

Cobicistat increased midazolam Cmax to the same extent on Day 7 and Day 10 and were approximately 5-fold higher compared to the corresponding values obtained following 1 mg Midazolam Alone on Day 5.

Cobicistat increased midazolam AUC∞ to the same extent on Day 7 and Day 10 and were approximately 25- to 27-fold higher compared to the corresponding values obtained following 1 mg Midazolam Alone on Day 5.

CONCLUSIONS

Cobicistat significantly increased systemic exposures of Compound A administered orally, via potent CYP3A inhibition, in healthy adult subjects. A single oral dose of Compound A, with steady state cobicistat, appeared generally safe and well tolerated by the healthy adult subjects in this study.

What is claimed is:

1. A method for increasing the plasma concentration of methyl 3-((methylsulfonyl)amino)-2-(((4-phenylcyclohexyl)oxy)methyl) piperidine-1-carboxylate, an optically active compound thereof, or a salt thereof, comprising administering to a subject (a) methyl 3-((methylsulfonyl) amino)-2-(((4-phenylcyclohexyl)oxy)methyl) piperidine-1-carboxylate, an optically active compound thereof, or a salt thereof; and (b) a CYP3A4 inhibitor.

2. A method for increasing wakefulness or decreasing excessive sleepiness in a subject in need thereof, comprising administering to the subject (a) methyl 3-((methylsulfonyl) amino)-2-(((4-phenylcyclohexyl)oxy)methyl) piperidine-1-carboxylate, an optically active compound thereof, or a salt thereof; and (b) a CYP3A4 inhibitor.

3. The method of claim 1, wherein the CYP3A4 inhibitor is selected from the group consisting of ritonavir and cobicistat.

4. The method of claim 1, wherein the CYP3A4 inhibitor is cobicistat.

5. The method of claim 1, wherein (a) is administered via oral administration.

6. The method of claim 1, wherein (a) is administered daily.

7. The method of claim 6, wherein (a) is administered as a single daily dose or multiple daily doses.

8. The method of claim 1, wherein the CYP3A4 inhibitor is administered daily.

9. The method of claim 8, wherein the CYP3A4 inhibitor is administered as a single daily dose or multiple daily doses.

10. The method of claim 1, wherein the CYP3A4 inhibitor is administered after administration of (a).

11. The method of claim 1, wherein the CYP3A4 inhibitor is administered before administration of (a).

12. The method of claim 1, wherein the CYP3A4 inhibitor is administered simultaneously with (a).

13. The method of claim 1, wherein (a) is an optically active compound.

14. The method of claim 13, wherein (a) is methyl (2R,3S)-3-((methylsulfonyl)amino)-2-(((cis-4-phenylcyclo-hexyl)oxy)methyl) piperidine-1-carboxylate or a salt thereof.

15. A composition comprising (a) methyl 3-((methylsulfo-nyl)amino)-2-(((4-phenylcyclohexyl)oxy)methyl) piperi-dine-1-carboxylate, an optically active compound thereof, or a salt thereof, and (b a CYP3A4 inhibitor.

16. The composition of claim 15, wherein the CYP3A4 inhibitor is selected from the group consisting of ritonavir and cobicistat.

17. The composition of claim 15, wherein (a) is an optically active compound.

18. The composition of claim 17, wherein (a) is methyl (2R,3S)-3-((methylsulfonyl)amino)-2-(((cis-4-phenylcyclo-hexyl)oxy)methyl) piperidine-1-carboxylate or a salt thereof.

* * * * *